United States Patent
Blasetti et al.

(10) Patent No.: US 6,398,972 B1
(45) Date of Patent: Jun. 4, 2002

(54) METHOD FOR PRODUCING PLATELET RICH PLASMA AND/OR PLATELET CONCENTRATE

(75) Inventors: Lou Blasetti, North Quincy; Sherwin V. Kevy, Brookline, both of MA (US)

(73) Assignee: Harvest Technologies Corporation, Plymouth, MA (US)

( * ) Notice: Subject to any disclaimer, the term of this patent is extended or adjusted under 35 U.S.C. 154(b) by 0 days.

(21) Appl. No.: 09/582,730

(22) PCT Filed: Apr. 11, 2000

(86) PCT No.: PCT/US00/08718

§ 371 (c)(1),
(2), (4) Date: Jun. 30, 2000

(87) PCT Pub. No.: WO00/61256

PCT Pub. Date: Oct. 19, 2000

Related U.S. Application Data

(60) Provisional application No. 60/128,800, filed on Apr. 12, 1999.

(51) Int. Cl.[7] .............................. B01D 21/26; B04B 5/02
(52) U.S. Cl. ...................... 210/782; 210/789; 210/806; 494/20; 494/37
(58) Field of Search .............................. 210/252, 512.1, 210/513, 782, 787, 789, 800, 806; 494/16, 17, 20, 32, 33, 35, 37, 43, 44, 85; 604/4.01, 5.01, 6.02, 6.04, 6.07

(56) References Cited

U.S. PATENT DOCUMENTS

| | | |
|---|---|---|
| 1,722,396 A | 7/1929 | Reiber |
| 3,190,546 A | 6/1965 | Raccuglia et al. |
| 3,420,437 A | 1/1969 | Blum et al. |
| 3,586,484 A | 6/1971 | Anderson |
| 3,642,163 A | 2/1972 | McFarland |
| 3,712,535 A | 1/1973 | Genese et al. |
| 3,722,789 A | 3/1973 | Kennedy |
| 3,774,455 A | 11/1973 | Seidler et al. |
| 3,851,817 A | 12/1974 | Buck |
| 3,859,671 A | 1/1975 | Tomasello |
| 3,877,634 A | 4/1975 | Rohde et al. |
| 3,951,334 A | 4/1976 | Fleming et al. |
| 3,953,172 A | 4/1976 | Shapiro et al. |
| 4,026,433 A | 5/1977 | Crippa |
| 4,066,407 A | 1/1978 | Lupica |
| 4,146,172 A | 3/1979 | Cullis et al. ................... 233/26 |
| 4,150,089 A | 4/1979 | Linet |
| 4,285,463 A | 8/1981 | Intengan |
| 4,294,372 A | 10/1981 | Onishi |
| 4,431,423 A | 2/1984 | Weyant, Jr. |
| 4,447,415 A | 5/1984 | Rock et al. |
| 4,714,457 A | 12/1987 | Alterbaum |
| 4,932,546 A | 6/1990 | Stannard |
| 4,985,153 A | 1/1991 | Kuroda et al. ............... 210/782 |
| 5,045,047 A | 9/1991 | Hutchins et al. .............. 494/17 |
| 5,047,004 A | 9/1991 | Wells ........................... 494/17 |
| 5,089,146 A | 2/1992 | Carmen et al. ............. 210/782 |
| 5,178,602 A | 1/1993 | Wells ........................... 494/17 |
| 5,209,776 A | 5/1993 | Bass et al. |
| 5,292,362 A | 3/1994 | Bass et al. |
| 5,318,524 A | 6/1994 | Morse et al. |
| 5,447,245 A | 9/1995 | Merhar |
| 5,503,284 A | 4/1996 | Li |
| 5,707,331 A | 1/1998 | Wells et al. ................... 494/20 |

FOREIGN PATENT DOCUMENTS

| | | |
|---|---|---|
| CA | 461698 | 12/1949 |
| FR | 0936560 | 7/1948 |

*Primary Examiner*—John Kim
(74) *Attorney, Agent, or Firm*—Clark & Brody

(57) ABSTRACT

Platelet rich plasma and/or platelet concentrate is prepared by placing whole blood in a first chamber of a sterile processing disposable having two chambers. The processing disposable is subjected to a first centrifugation to separate red blood cells, and the resulting platelet rich plasma supernatant is decanted to the second chamber. The processing disposable is subjected to a second centrifugation to concentrate platelets. A volume of the platelet poor plasma supernatant in the second chamber is removed, and the platelets are re-suspended in the remaining plasma. The second chamber may contain anticoagulant to preclude aggregation of the platelets.

10 Claims, 2 Drawing Sheets

METHOD FOR PRODUCING PLATELET RICH PLASMA AND/OR PLATELET CONCENTRATE

This application is a 371 of PCT/US00/08718 filed Apr. 11, 2000 which claims benefit of Provisional No. 60/128,800 filed Apr. 12, 1999.

TECHNICAL FIELD

This invention relates to the art of methods and apparatus for producing platelet rich plasma or a platelet concentrate. In particular, the invention relates to automated, highly efficient methods for separating platelets and plasma and for combining these in a selected proportion to provide platelet rich plasma or platelet concentrate of selected concentration.

BACKGROUND

Common methods for producing platelet rich plasma (PRP) involve a "gentle" centrifugation of whole blood. Platelet concentrate (PC) results from a second centrifugation of the PRP.

The platelets in platelet rich plasma PRP or platelet concentrate (PC) posses granules that contain growth factors (e.g., PDGF, TGF-β, and others), which aid in accelerating angiogenesis (wound healing) and osteogenesis (bone growth). PRP/PC, when combined with thrombin, may also be used adjunctively to control bleeding (hemostasis), seal wounds, and as a vehicle for the delivery of drugs and/or biological agents. Further, the handling characteristics of certain organic materials, such as bone powder, can be greatly improved by combining them with PRP/PC, with or without the addition of thrombin. Such a combination also provides more secure placement of organic materials, for example, into an orthopedic defect. Some properties of PRP/PC and thrombin (e.g., hemostasis and wound sealing) are similar to those of fibrin glue, except that fibrin glue has a greater adhesive property because of its concentration of fibrinogen above baseline levels.

A typical method of producing PC involves subjecting whole blood collected in a blood bag system to centrifugation to separate PRP from red blood cells. Then, the PRP is expressed from the first bag to a second bag and again subjected to centrifugation, which results in a concentration ("peller") of platelets (PC) and a supernatant of platelet poor plasma (PPP). The majority of the PPP is expressed to a third bag, leaving the concentrated platelets and a small proportion of PPP behind in the second bag, which is used for re-suspending the concentrated platelets. This method, with a typical platelet recovery efficiency of only 45%, is too cumbersome for point-of-care use and, as a result, does not lend itself to point-of-care production of autologous blood products.

One automated system for the production of autologous fibrinogen from plasma is known from U.S. Pat. No. 5,707,331 (Wells). That patent teaches a system for automated processing of whole blood by centrifugation into a plasma component that is further processed by physiochemical precipitation and further centrifugation into a fibrinogen component. The fibrinogen is recovered and provides a fibrin sealant when combined with thrombin.

The ability to produce PRP/PC on demand from small amounts of whole blood would greatly facilitate clinical utility of PRP/PC, and availability of autologous PRP/PC would eliminate the need for homologous PRP/PC, which may carry the risk of transmitting human disease. Further, it is often desirable to provide PRP/PC of a selected concentration to achieve a particular therapeutic outcome. However, the known methods presently used for producing PRP/PC are time consuming, inefficient, and do not lend themselves to production from small amounts of whole blood.

Accordingly, it is an object of this invention to provide a method and apparatus for processing efficiently small volumes of whole blood into PRP or PC of any selected concentration on demand, at the point of care, and in the clinical setting.

SUMMARY OF THE INVENTION

In accordance with the invention, small amounts of PRP or PC are easily produced by an automated method preferably carried out by a centrifuge such as that shown in U.S. Pat. No. 5,707,331 (Wells). The centrifuge shown in the '331 Wells patent receives a disposable container, or processing disposable (PD), having two chambers, and in the method of the present invention, whole blood is first placed in one chamber of the PD. The centrifuge is then operated to cause the red blood cells to sediment to the bottom of one chamber resulting in a supernatant of PRP. The centrifugation is stopped/reduced causing the PRP to drain to the second chamber, either by gravity or by centrifugal transfer.

PRP in the second chamber is then centrifuged a second time by restarting/accelerating the centrifuge. The centrifuge is then stopped, resulting in: (1) red blood cells in the one chamber, (2) platelets (PC) at the bottom of the second chamber, and (3) platelet poor plasma (PPP) as the supernatant in the second chamber. The foregoing operation of the centrifuge is preferably automated.

The operator may then produce PRP/PC of a desired concentration by obtaining a prescribed volume of the plasma supernatant and re-suspending the platelets.

In a preferred embodiment, the operator inserts a blunt cannula attached to a syringe into the second chamber and withdraws a desired volume of plasma, which leaves behind a known volume of plasma. A second blunt cannula attached to a syringe is then inserted into the second chamber where the remaining known volume of plasma is used to re-suspend and recover the PRP/PC having increased platelet concentration.

There may be other ways to recover the platelets and plasma. For example, after completion of the automated steps, the operator could decant plasma from the second chamber by tilting the disposable container to cause an amount of plasma to return to the first chamber, leaving the desired amount of plasma in the second chamber. The remaining plasma and the platelets would then be mixed and recovered.

In one example, a patient's whole blood sample is obtained, containing a typical platelet count of $220 \times 10^3/\mu l$. Based on a typical platelet recovery efficiency of 60% and processing a typical blood volume of 50 ml, re-suspending the PC in 5 ml of PPP will provide PRP with a platelet concentration of $1,320 \times 10^3/\mu l$, a six-fold increase in the platelet concentration.

DETAILED DESCRIPTION OF THE PREFERRED EMBODIMENT

Figure 1:
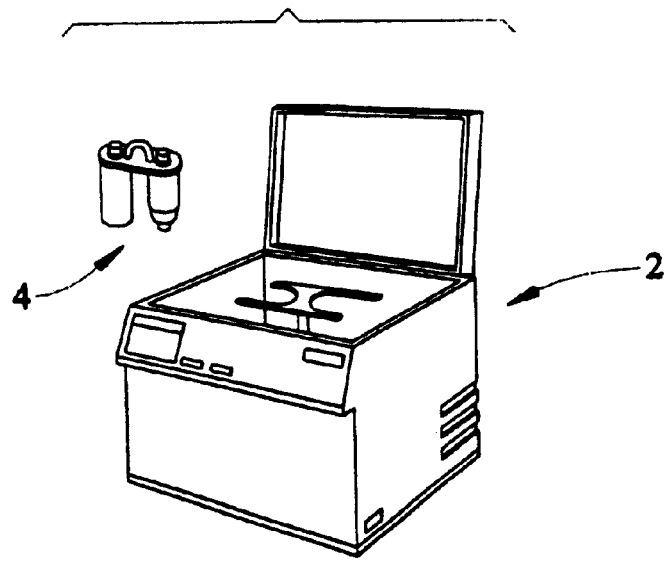
FIG. 1 illustrates a disposable processing tube and centrifuge in accordance with the invention.

FIG. 1 schematically illustrates a centrifuge system 2 and a processing disposable (PD) 4 in accordance with the invention. The preferred centrifuge is that described in U.S. Pat. No. 5,707,331 (Wells) programmed to operate as will be described in connection with FIG. 3. As will be appreciated, the rotor of the centrifuge 2 is designed to accept one or more PDs 4 simultaneously. In the preferred embodiment, the centrifuge accepts one or two PDs. A counterweight is placed opposite a filled PD when only one is used.

Figure 2:
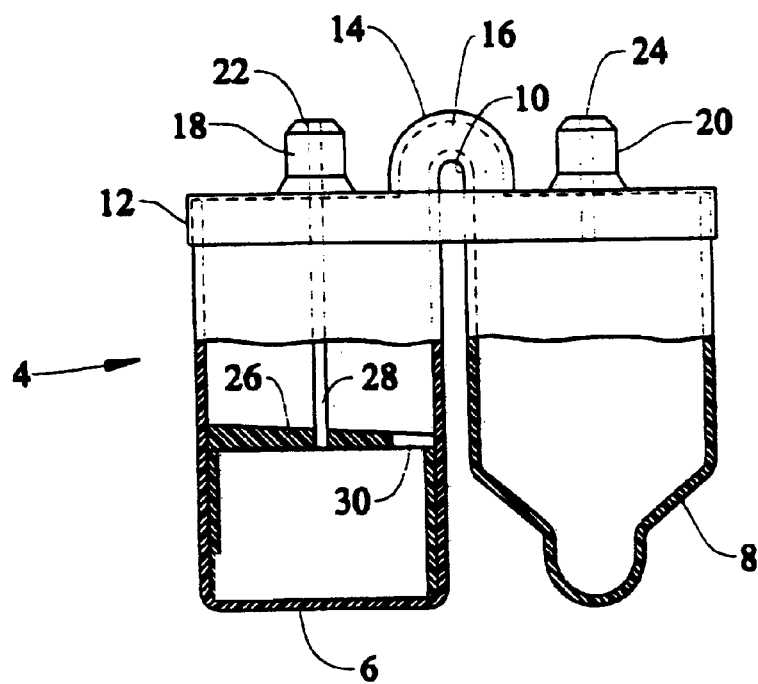
FIG. 2 is a side view of the processing tube shown in FIG. 1, partly in vertical cross section.

The PD used in accordance with the invention and shown in FIG. 2 is that shown in the noted '331 patent. This PD is preferably made of molded plastic and includes at least two chambers 6, 8. The two chambers are connected by a bridge 10, which connects the two chambers, preferably, at their tops. The chambers are closed by a lid 12, which maintains sterility of the fluid paths.

The lid includes extensions 18 and 20 having respective openings 22 and 24 for permitting access to the interior of the chambers. Chamber 6 includes a shelf 26 for assisting in the separation of PRP from cellular components, as will be described in more detail below. Chamber 6 also includes a hollow tube 28, which extends from the opening 22 through the shelf 26 to facilitate insertion of fluids into the chamber 6. The perimeter of the shelf allows plasma below the shelf 26 to flow upward.

Figure 3A:
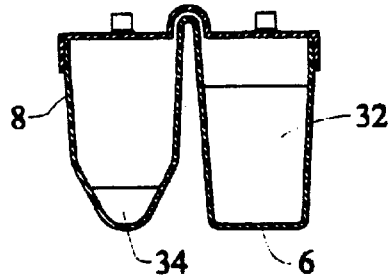
FIGS. 3a through 3f are schematic cross sections of the processing tube of FIG. 2 showing the various orientations
Figure 3B:
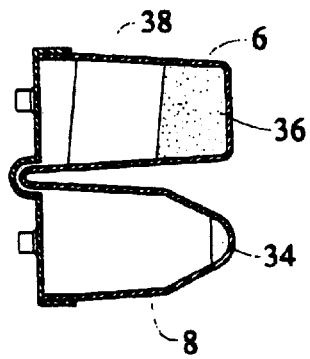

Referring now to FIGS. 3a through 3f, the operation of the centrifuge 2 in accordance with the process of the invention will be described. In the first step of the process, chamber 6 of the PD 4 is provided with a measured quantity of a physiological fluid 32 to be processed, such as whole human blood. A quantity (e.g., 1–5 ml and preferably 2 ml) of anticoagulant 34, preferably ACD-A, is added to chamber 8. Then, the PD is subjected to centrifugation as illustrated in FIG. 3b. This separates heavier components of the physiological fluids, such as red blood cells 36, from the supernatant, such as PRP 38. The ACD-A 34 remains in chamber 8.

The first centrifugation illustrated in FIG. 3b causes the red blood cells to separate from the PRP but does not significantly separate platelets from the remainder of the plasma. In the preferred embodiment, this first centrifugation is done at about 1200 G (approximately 3600 RPM) for a period of about two minutes.

For clarity FIGS. 3a through 3f do not illustrate the shelf 26, but it should be noted that in the preferred embodiment, the shelf is located as close as possible to the boundary between the separated components, namely the red blood cells 36 and the plasma 38. The preferred method for accomplishing this is to determine the concentration of red blood cells in the patient's blood (i.e., the hematocrit) and to provide a quantity of blood that will fill the volume below the shelf with the red blood cells. Preferably, the chamber 6 is designed to accept 50 ml of patient's blood as the nominal volume. This amount is adjusted during operation of the equipment in accordance with the hematocrit, and applicants have found that the volume of whole blood required will be in the range of 40 ml–60 ml.

Figure 3C:
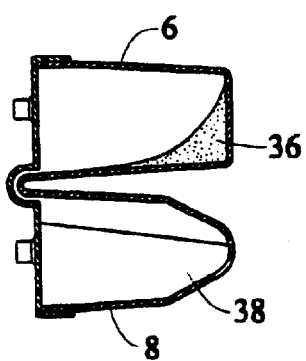

After the red blood cells have been centrifugally separated, the PD is locked in the gravity drain position shown in FIG. 3c. This is described further in the '311 Wells patent and is preferably done by electrical activation of a magnet that moves a locking plate into engagement with a holder having the PD therein. When the PD is in this position, the PRP 38 in chamber 6 drains into the chamber 8 by gravity. For example, 25 ml of PRP is transferred to chamber 8. The PRP 38 also mixes with the ACD-A 34, previously in chamber 8, as it flows into the chamber through the flow channel 16.

It is often desirable during the draining step shown in FIG. 3c to continue rotation of the rotor at a slow speed, e.g., 60 RPM, to provide a slight centrifugal force to ensure retention of the red blood cells 36 in the chamber 6.

Figure 3D:
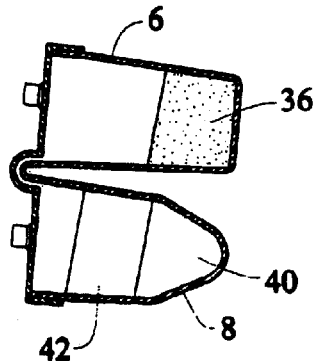

As illustrated in FIG. 3d, the centrifuge is then accelerated again to subject the PRP 38 to centrifugation. The second centrifugation separates platelets 40 from the PPP supernatant 42. In the preferred embodiment, the second centrifugation is at about 1000 G (approximately 3000 RPM) for a period of about eight minutes.

It will be appreciated that the specific rotation rates for the first and second centrifugation steps can be varied. For example, the second centrifugation can be a hard spin. Also, the disclosed preferred rates are for a centrifuge having a maximum rotor radius of four inches (i.e., the radius of rotation measured from the axis to the bottom of the chamber). Centrifuges with other dimensions will require different rotation rates.

The ACD-A is provided in the chamber 8 for minimizing platelet aggregation. It has been found that the presence of an anticoagulant in the second chamber reduces aggregation of the platelets, thus shortening the overall time required for processing.

Figure 3E:
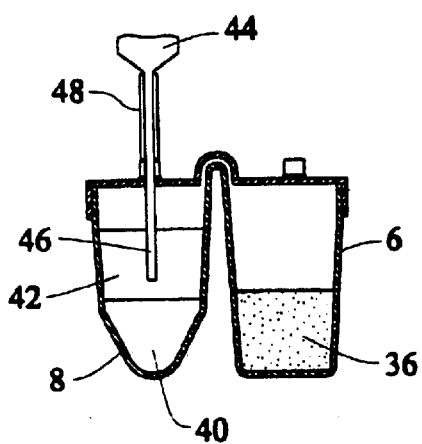

The next step in the process of the invention is shown in FIG. 3e. In this step, the centrifugation has been stopped, and the PD is allowed to assume an upright orientation, with the red blood cells 36 remaining in chamber 6, the platelets 40 at the bottom of chamber 8, and the PPP 42 as the supernatant in chamber 8. A hypodermic syringe 44 with a blunt cannula 46 is used for removing a predetermined amount of PPP. This is accomplished by inserting the blunt cannula through the opening 24 to a predetermined depth. The operator may determine that depth manually, or, as shown in FIG. 3e, a height adjusting guide 48 may be provided over the cannula to stop insertion at the desired depth. The guide may take any of several forms, the preferred form being a hollow tube that fits over the cannula and engages the bottom of the syringe. Also, a kit having a plurality of such guides of different lengths may be provided for allowing the operator to select one for withdrawal of different, predetermined amounts of PPP.

It will be appreciated that the described use of cannula 46 with height adjusting guide 48 removes from the chamber 8 a predetermined amount of fluid that in this case is equal to the difference between the volume of fluid in the chamber initially and the desired volume of fluid as defined by the height of the guide 48.

Further, removal of a desired amount of PPP may be accomplished by decanting some of the plasma back to chamber 6, either manually or by centrifugal transfer using the multiple-decanting features of the centrifuge described in the '331 Wells patent.

Continuing with the process shown in FIG. 3e, the syringe is operated after insertion of the cannula 46 to the desired depth to withdraw the desired amount of PPP, which is then used for other purposes, such as hemostasis.

Figure 3F:
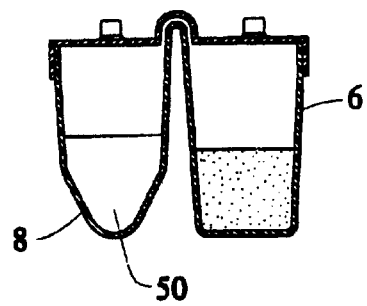

As shown in FIG. 3f, the platelets 40 are then re-suspended in the remaining PPP to result in PRP/PC 50 with a desired platelet concentration that is several times higher than was the original supernatant 38. This PRP/PC of increased concentration is then used for any of a variety of purposes as are known in the art.

Modifications within the scope of the appended claims will be apparent to those of skill in the art.

We claim:

1. A method for producing a physiological product of selected composition comprising the steps of:

placing a physiological fluid having a plurality of components in a first chamber of a rigid sterile container having horizontally spaced first and second chambers;

subjecting said physiological fluid to centrifugation to separate at least one of said components from a first supernatant;

decanting said first supernatant to said second chamber;

subjecting said first supernatant to centrifugation to separate a second of said components from a second supernatant;

removing a predetermined amount of said second supernatant from said second chamber whereby a remainder of said second supernatant is in said second chamber; and re-suspending said second of said components in said remainder of said second supernatant in said second chamber.

2. A method according to claim 1 further comprising the step of placing anticoagulant in said second chamber.

3. A method according to claim 1 wherein said physiological fluid is blood.

4. A method according to claim 3 wherein said physiological product is platelet rich plasma and said step of subjecting said physiological fluid to centrifugation comprises subjecting blood to a first centrifugation for about two minutes.

5. A method according to claim 4 wherein said step of subjecting said first supernatant to centrifugation comprises subjecting platelet rich plasma to a second centrifugation for about eight minutes.

6. A method according to claim 1 wherein said step of removing comprises inserting a cannula into said second chamber and withdrawing said predetermined amount of second supernatant through said cannula.

7. A method according to claim 1 wherein said predetermined amount is the volume of said second supernatant in said second chamber that exceeds a desired volume in said second chamber.

8. A method for making platelet rich plasma at point of care comprising the steps of placing blood in a first chamber of a sterile container having first and second chambers, wherein at least said second chamber is rigid and of defined volume, subjecting said container and blood to centrifugation to provide a supernatant comprising platelet rich plasma, transferring said platelet rich plasma from said first chamber to said second chamber, subjecting said platelet rich plasma to centrifugation to provide separated platelets and platelet poor plasma, removing a portion of said platelet poor plasma from said second chamber and leaving a remaining portion of said platelet poor plasma and said separated platelets in said second chamber, and suspending said separated platelets in said remaining portion of said platelet poor plasma to obtain said platelet rich plasma.

9. A method according to claim 8 further comprising the step of placing an anticoagulant in said second chamber.

10. A method according to claim 8 wherein said step of removing comprises inserting a cannula into said second chamber and withdrawing said portion of platelet poor plasma.

\* \* \* \* \*